United States Patent
Lee et al.

(10) Patent No.: US 10,022,412 B2
(45) Date of Patent: Jul. 17, 2018

(54) COMPOSITION FOR PREVENTING OR ALLEVIATING PERIODONTAL DISEASES, CONTAINING, AS ACTIVE INGREDIENT, MANGOSTEEN EXTRACT OR α- OR γ-MANGOSTEEN

(71) Applicant: Medi Bio Lab. co., Ltd., Daejeon (KR)

(72) Inventors: Dae Sung Lee, Seoul (KR); Yoon Seok Ko, Geoje-si (KR); Chan Ho Kim, Gwangju (KR); Min Jung Ryu, Daegu (KR); Young Jin Kim, Busan (KR); Ik Jin In, Gimhae-si (KR); Sung Kwon Lee, Seoul (KR)

(73) Assignee: MEDI BIO LAB. CO., LTD., Daejeon (KR)

( * ) Notice: Subject to any disclaimer, the term of this patent is extended or adjusted under 35 U.S.C. 154(b) by 0 days.

(21) Appl. No.: 15/510,384

(22) PCT Filed: Sep. 16, 2015

(86) PCT No.: PCT/KR2015/009734
§ 371 (c)(1),
(2) Date: Mar. 10, 2017

(87) PCT Pub. No.: WO2016/043524
PCT Pub. Date: Mar. 24, 2016

(65) Prior Publication Data
US 2017/0296604 A1    Oct. 19, 2017

(30) Foreign Application Priority Data

Sep. 16, 2014 (KR) .................. 10-2014-0122945

(51) Int. Cl.
| | | |
|---|---|---|
| A61K 36/38 | (2006.01) | |
| A61K 8/11 | (2006.01) | |
| A61K 38/47 | (2006.01) | |
| A61K 36/48 | (2006.01) | |
| A61K 35/644 | (2015.01) | |
| A61K 31/375 | (2006.01) | |
| A61K 31/355 | (2006.01) | |
| A61K 31/352 | (2006.01) | |
| A61K 31/047 | (2006.01) | |
| A61K 9/48 | (2006.01) | |
| A61K 8/98 | (2006.01) | |
| A61K 8/97 | (2017.01) | |
| A61K 8/73 | (2006.01) | |
| A61K 8/67 | (2006.01) | |
| A61K 8/66 | (2006.01) | |
| A61K 8/49 | (2006.01) | |
| A61K 8/34 | (2006.01) | |
| A61K 47/40 | (2006.01) | |

(52) U.S. Cl.
CPC .............. *A61K 36/38* (2013.01); *A61K 8/11* (2013.01); *A61K 8/345* (2013.01); *A61K 8/498* (2013.01); *A61K 8/66* (2013.01); *A61K 8/676* (2013.01); *A61K 8/678* (2013.01); *A61K 8/738* (2013.01); *A61K 8/97* (2013.01); *A61K 8/988* (2013.01); *A61K 9/48* (2013.01); *A61K 31/047* (2013.01); *A61K 31/352* (2013.01); *A61K 31/355* (2013.01); *A61K 31/375* (2013.01); *A61K 35/644* (2013.01); *A61K 36/48* (2013.01); *A61K 38/47* (2013.01); *A61K 47/40* (2013.01); *A61K 2236/33* (2013.01)

(58) Field of Classification Search
None
See application file for complete search history.

(56) References Cited

U.S. PATENT DOCUMENTS

| | | | | |
|---|---|---|---|---|
| 2005/0266018 A1* | 12/2005 | Boreyko | ................ | A61K 33/04 424/195.17 |
| 2010/0196542 A1* | 8/2010 | Boursier | ............... | A23L 1/0522 426/72 |
| 2010/0330137 A1* | 12/2010 | Mantovani | ........... | A61K 9/1652 424/401 |
| 2012/0237456 A1* | 9/2012 | Trivedi | .................... | A61K 8/97 424/48 |

FOREIGN PATENT DOCUMENTS

| | | |
|---|---|---|
| JP | 04-244004 | 9/1992 |
| JP | 05-17365 | 1/1993 |
| JP | 06-98738 | 4/1994 |
| JP | 07-147951 | 6/1995 |

(Continued)

OTHER PUBLICATIONS

Miri Park et al., "Antibacterial Activity of [10]-Gingerol and [12]-Gingerol isolated from Ginger Rhizome Against Periodontal Bacteria", Phytother. Res. 22, 1446-1449, Sep. 23, 2008.

Mingyu Li and Zhuting Xu, "Quercetin in a Lotus Leaves Extract May be Responsible for Antibacterial Activity", Arch. Pharm. Res. vol. 31, No. 5, 640-644, May 15, 2008.

Julia Cazalis and Charles Bodet et al., "Doxycycline Reduces Lipopolysaccharide-Induced Inflammatory Mediator Secretion in Macrophage and Ex Vivo Human Whole Blood Models", J. Periodontal. vol. 9, No. 9, Sep. 2008—Abstract only.

(Continued)

*Primary Examiner* — Robert A Wax
*Assistant Examiner* — Danah Al-Awadi
(74) *Attorney, Agent, or Firm* — Lex IP Meister, PLLC

(57) ABSTRACT

The present invention provides a composition for preventing, improving or treating periodontal diseases comprising extract of mangosteen.

The composition of the present invention has excellent anti-bacterial and anti-inflammatory effects against bacteria inducing periodontal diseases as comprising extract of mangosteen, or alpha-mangosteen or gamma-mangosteen derived from thereof, and thereby it can be widely used for medicines and foods for preventing, improving or treating periodontal diseases.

6 Claims, 5 Drawing Sheets

(56) References Cited

FOREIGN PATENT DOCUMENTS

| | | |
|---|---|---|
| JP | 07-250658 | 10/1995 |
| JP | 08-208501 | 8/1996 |
| JP | 09-87155 | 3/1997 |
| JP | 10-72357 | 3/1998 |
| JP | 10-120586 | 5/1998 |
| JP | 11-323247 | 11/1999 |
| JP | 11-343247 | 12/1999 |
| JP | 2001-247469 | 9/2001 |
| JP | 2002-047180 | 2/2002 |
| JP | 2003-231607 | 8/2003 |
| JP | 2004-194554 | 7/2004 |
| JP | 2008-127304 | 6/2008 |
| KR | 10-2011-0060154 | 6/2011 |

OTHER PUBLICATIONS

Phunog T. M. Nguyen et al., "Antimicrobial actions of a-mangostin against oral *streprococci*", Can. J. Microbiol., 2011, vol. 57, pp. 217-225.

\* cited by examiner

[Fig. 1]
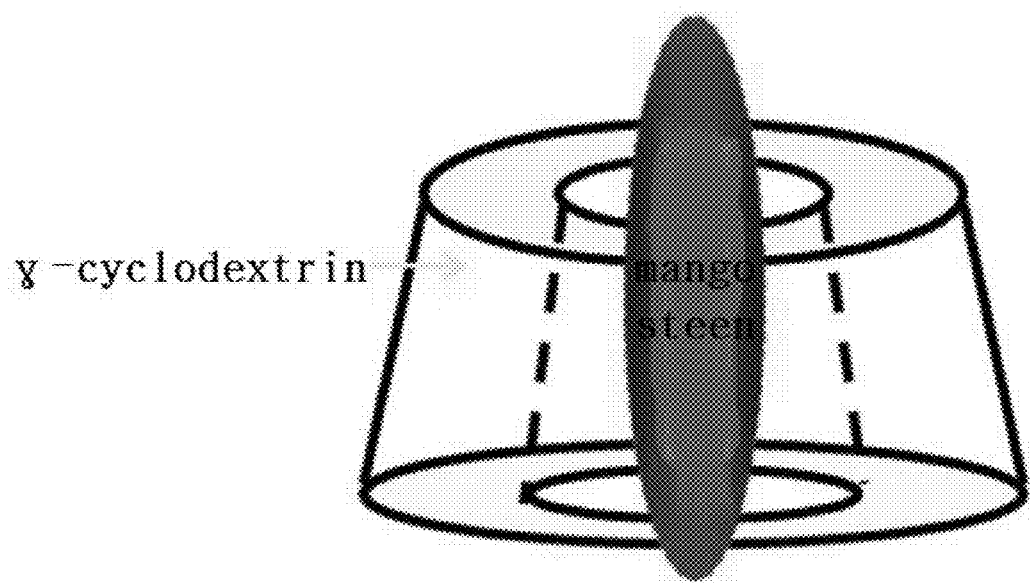

[Fig. 2]
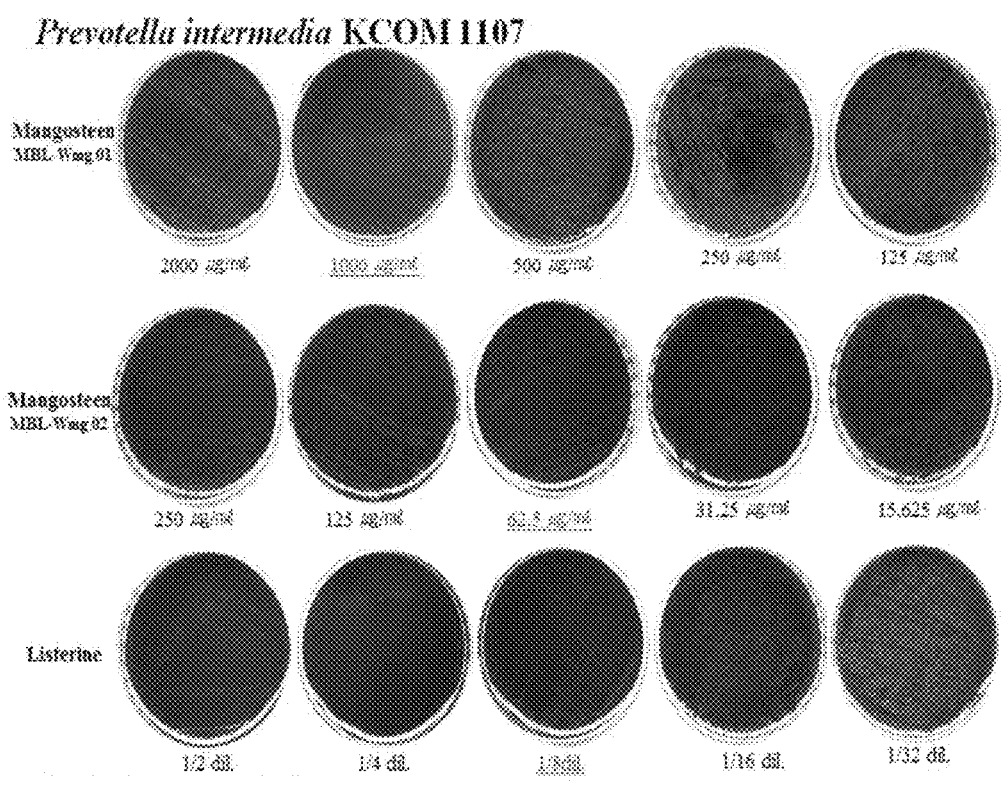

[Fig. 3]
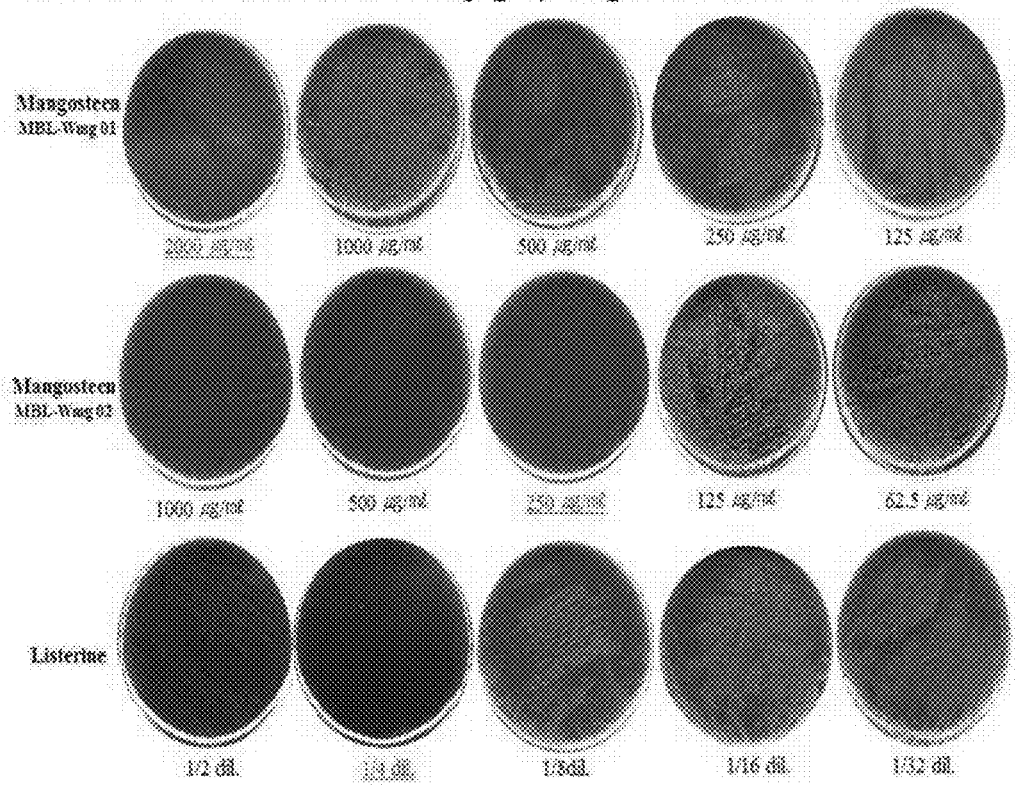
\* Red letters refer to MBC value

[Fig. 4]
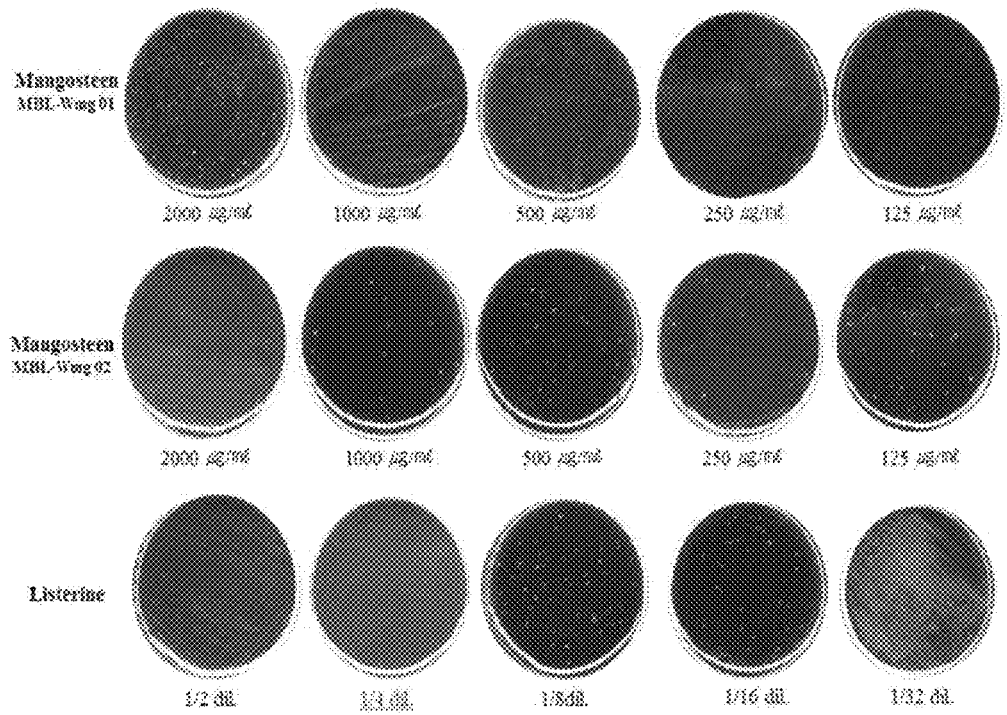
* Red letters refer to MBC value

[Fig. 5]
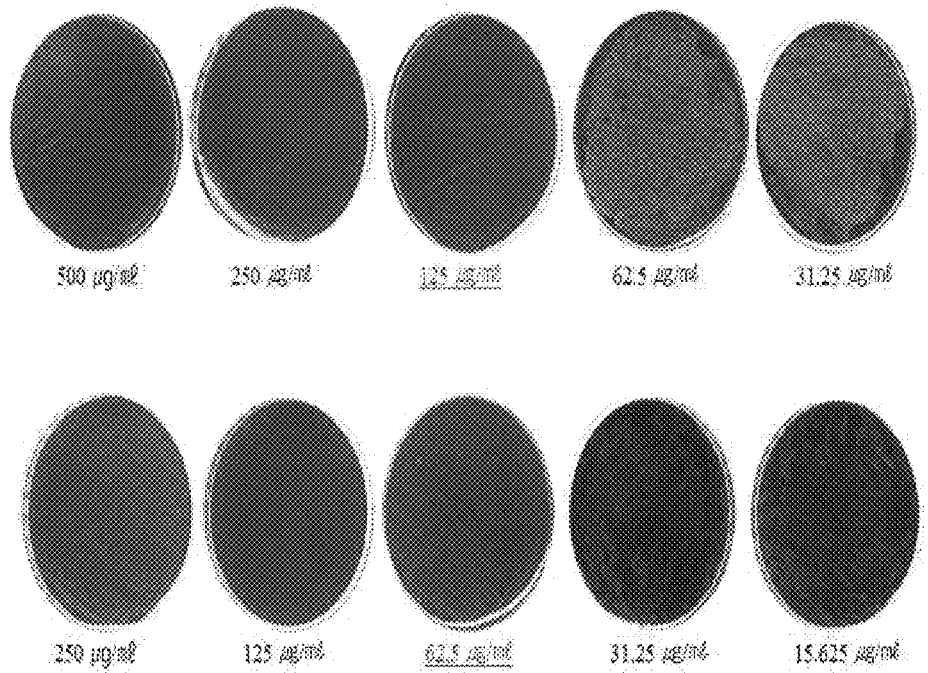
\* Red letters refer to MBC value

COMPOSITION FOR PREVENTING OR ALLEVIATING PERIODONTAL DISEASES, CONTAINING, AS ACTIVE INGREDIENT, MANGOSTEEN EXTRACT OR α- OR γ-MANGOSTEEN

TECHNICAL FIELD

The present invention relates to a composition for improving or preventing periodontal diseases comprising extract of mangosteen having an excellent anti-inflammatory effect or its active ingredient.

BACKGROUND ART

A periodontal disease is often referred as Pungchi, and it means an inflammatory disease accompanying destruction of periodontal tissues caused by bacterial complex infection (mixed infection). It shows various clinical symptoms such as gingival bleeding and swelling, formation of periodontal pocket, loss of attached gingival, destruct ion of alveolar bone, and bad breath, and it is becoming a major cause of tooth loss and implant failure.

Such periodontal disease is a very different disease in aspects of oral tissues occurred, causative organisms, and onset mechanism, compared to dental caries which is generally called cavity. Specifically, dental caries occurs on tooth, and a periodontal disease occurs in periodontal tissues (cement, gingival, periodontal ligament, alveolar bone). The causative organisms of dental caries are bacterial species expressing organic acids (mainly lactic acid) by carbohydrate fermentation metabolism including mutans group streptococcus, while a periodontal disease mainly occurs by gram negative anaerobic bacteria. In other words, dental caries is occurred in an acidic condition, whereas a periodontal disease is occurred in a basic condition. That is because nitrogen metabolism occurs more actively than carbohydrate metabolism in gram negative anaerobic bacteria. Thereby, tartar is built a lot in the region where a periodontal disease occurs.

Such periodontal disease is known to generally occur by various topical and systemic factors, and the most important one of topical factors is a dental plaque, which is known as up to now about 500 bacterial species exist in the dental plaque and they form a kind of biofilm. Among such bacterial species, major causative organisms of periodontal diseases include *Fusobacterium nucleatum*, and *Porphyromonas gingivalis, Prevotella intermedia, Parvimonas micra* (also called *Peptostreptococcus micros*), and *Aggregatibacter actinomycetemcomitans* (also called *Actinobacillus actinomycetemcomitans*), etc.

An innate immune response and destruction mechanism of alveolar bone by such pathogenic bacteria of periodontal diseases are as follows.

Human gingival epithelial cells primarily act as physical barriers to prevent bacterial invasion, and secret anti-bacterial peptides (human beta defensins and LL-37 etc.). Thus, as a result of susceptibility investigation to anti-bacterial peptides secreted from human gingival epithelia, defensins and LL-37, it is reported that strongly pathogenic bacterial species (*P. gingivalis* and *P. intermedia*) are highly susceptible to the anti-bacterial peptides, while low pathogenic bacterial species (*S. mutans* etc.) and *F. nucleatum* are killed at a low concentration.

In addition, human gingival epithelial cells secret cytokines and chemokines like Interleukin-8(IL-8) and IL-1α, etc. by causative organisms of periodontal diseases, thereby inducing innate immune responses and removing those bacteria. If a primary barrier, gingival epithelial cells are destroyed by oral microorganisms in a dental plaque, adaptive immune responses as well as innate immune responses are activated, and in case of not removing pathogens, destruction of periodontal tissues is accelerated.

Also, the continuity of gingival epithelia is protected by neutrophils and antibodies from bacterial infection. Specifically, bacterial toxins are neutralized by antibodies and bacteria become opsonized (opsonization) by complement activity, thereby bacteria are removed by macrophages. However, when the continuity of gingival epithelial cells is destroyed, bacteria or bacterial products [LPS, phosphoryl choline, proteasleukotoxin, cytolethal distendingtoxin (CDT), etc.] are introduced in periodontal tissues, thereby inducing immune responses, and immune mediated molecules such as interleukin(IL)-1, IL-6, prostaglandinE2 (PGE2) and tumor necrosis factor(TNF)-α, etc. are secreted by lymphocytes, macrophages, etc., and a receptor activator of nuclearfactor κB ligand(RANKL) osteoprotegerin(OPG) is secreted in gingival epithelial cells, periodontal ligament epithelial cells, preosteoblast, etc., thereby controlling differentiation of osteoclasts. Then, human periodontal ligament fibroblasts increases RANKL expression, reduces OPG expression by responding to IL-1, and promotes differentiation of preosteoclasts, thereby participating in destruction of alveolar bone.

On the other hand, gingival fibroblasts promote OPG expression by responding to IL-1, thereby inhibiting differentiation of preosteoclasts.

Meanwhile, LPS of *A. actinomycetemcomitans* combines to TLR-4 of periodontal ligament cells, activates p38 MARK pathway, and increases differentiation of preosteoclasts. *P. gingivalis* increases RANKL expression from periodontal ligament cells by Lys-gingipain.

However, even though periodontal diseases are occurred by mixed infection of various bacterial species, mostly only researches for innate immunity to single bacterial species are progressed.

Currently, the treatment of periodontal disease includes oral hygiene improvement of patients, non-surgical treatment and surgical treatment (dental plaque removal, root planning, gingival curettage, regeneration of periodontal tissues applied with new attachment). The most effective treatment, surgical treatment has inconvenience to go to the dentist for treatment and limitation of performing when a disease progresses in some degree rather than prevention of the disease. Therefore, as periodontal diseases are not effectively treated, periodontal diseases mostly become chronic. As additional treatments, systemic administration of antibiotics and local sustained release formulations have been used, but there are serious problems, as there have been reported side effects caused by delivering too many agents to unneeded regions and a case in which a periodontal disease bacterium is separated, which shows resistance to antibiotics.

In particular, in case of our country, according to "2013 Health Statistics Index" by Health Insurance Review & Assessment Service, the number of people who visited dentistry due to periodontal diseases increased by more than 10 million people, about twice that of 2004. Although a periodontal disease is a disease which people in our country are suffering except acute upper respiratory inflammation (common cold), there have been reported that drugs such as Igatan® and Insadol®, etc., which are currently known as representative therapeutic agents for periodontal diseases, actually do not have direct effects on periodontal diseases and are merely health food or supplements.

Researches have been carried out to investigate an antibacterial activity using natural plant extracts to develop alternative substances for complementing limitation of surgical treatments and problems of antibiotics use and enhancing effects of preventing and treating periodontal diseases For example, substances having antibacterial activities have been developed by measuring antibacterial activities to causative bacteria for periodontal diseases in nature extracts such as red ginger roots (Park et al., Phytother. Res. 22, 1446-1449, 2008), medicinal plants of South Africa, lotus leaves (Li and Xu, Arch. Pharm. Res. Vol 31, No. 5, 640-644, 2008), etc., and recently, it is demonstrated that as treating GCSB-5, after injecting a substance isolated from licorice extracts with inflammatory substances iNOS and COX-2 to a lipopolysaccharide (LPS), which is an endotoxin substance existing in cell walls of *A. actinomycetemcomitans* and *P. gingivalis*, activation of intracellular messengers (Akt and NF-kB) which participate in inflammatory process reduces, thereby alleviating symptoms and edemas (Bodet et al., J. Periodontol. Vol. 9, No. 9, 2008). However, a therapeutic agent derived from nature plants or health functional foods which are effective against periodontal diseases are not commercially available so far.

Meanwhile, mangosteen (*Garcinia mangostana*) is a fruit of a dicotyledonous plant belonging to Sapindales pepper tree of origin of Malaysia and bear a slightly larger size of fruit than a flat ball-shaped table tennis ball. The fruit of mangosteen is known to have excellent antioxidant ability, since it contains a representative antioxidant component called xanthone, which is a kind of polyphenols. In the Southeast Asia including Thailand, it has been used as a folk drug a long time age, for treating inflammation or injuries like wounds, etc.

Further, as other uses of mangosteen, with respect to mangosteen pericarps, food preservatives in Japanese laid-open patent application No. 6-98738 and laid-open patent application No. 7-147951, 5α-reductase in laid-open patent application No. 5-17365, antibacterial agents in laid-open patent application No. 7-250658, anti-*helicobacter pylori* drugs in laid-open patent application No. 8-208501, ultraviolet absorbers in laid-open patent application No. 9-87155, and serine protease inhibitors in laid-open patent application No. 10-120586 are disclosed.

Also, with respect to water-soluble extracts of manhosteen pericarps, whitening and anti-inflammatory actions by inhibitory action of histamine isolation from mast cells are disclosed in Japanese laid-open patent application No. 4-244004. With respect to polar solvent extracts of mangosteen pericarps and alpha-mangosteen, gamma-mangosteen, anti-allergic actions by antagonism for histamine and serotonin are disclosed in Japanese laid-open patent application No. 10-72357. However, an effect regarding periodontal diseases of mangosteen extracts and substances isolated from thereof is not disclosed at all.

Under these backgrounds, the present inventors have intensively researched to develop pharmaceutical and food compositions having excellent effects on preventing, improving and treating periodontal diseases based on natural products. As a result, it is demonstrated that mangosteen extracts and alpha-mangosteen, gamma-mangosteen isolated from thereof have substantially excel lent antibacterial and anti-inflammatory effects against causative organisms for periodontal diseases, thereby completing the present invention.

DISCLOSURE

Technical Problem

A purpose of the present invention is to provide a pharmaceutical composition for preventing or treating periodontal diseases having excellent anti-bacterial and anti-inflammatory effects.

Another purpose of the present invention is to provide a food composition for preventing or improving periodontal diseases having excellent anti-bacterial and anti-inflammatory effects.

Technical Solution

As an aspect to achieve the above object, the present invention provides a pharmaceutical composition for preventing or treating periodontal diseases comprising extract of mangosteen.

As another aspect, the present invention provides a pharmaceutical composition for preventing or treating periodontal diseases comprising one or more selected from the group consisting of alpha-mangosteen and gamma-mangosteen.

As another aspect, the present invention provides a food composition for preventing or improving periodontal diseases comprising extract of mangosteen.

As another aspect, the present invention provides a food composition for preventing or improving periodontal diseases comprising one or more selected from the group consisting of alpha-mangosteen and gamma-mangosteen.

Advantageous Effects

The composition of the present invention has excel lent anti-bacterial and anti-inflammatory effects against bacteria inducing periodontal diseases as comprising extract of mangosteen, or alpha-mangosteen or gamma-mangosteen derived from thereof, and thereby it can be widely used for medicines and foods for preventing, improving or treating periodontal diseases.

DESCRIPTION OF DRAWINGS

FIG. 1 is a diagram of the structure in case of formulating the composition comprising mangosteen extracts according to the present invent ion to a nano capsule form.

FIG. 2 is a photograph showing MBC test results of mangosteen extracts which are comprised in the composition of the present invent ion to *Prevotella intermedia* KCOM 1107.

FIG. 3 is a photograph showing MBC test results of mangosteen extracts which are comprised in the composition of the present invention to *Fusobacterium nucleatum* subsp. *Polymorphum* KCOM 1232.

FIG. 4 is a photograph showing MBC test results of mangosteen extracts which are comprised in the composition of the present invention to *Aggregatibacter actinomycetemcomitans* KCOM 1306.

FIG. 5 is a photograph showing MBC test results of mangosteen extracts which are comprised in the composition of the present invention to *Porphyromonas gingivalis* ATCC 33277T.

BEST MODE

Hereinafter, the present invention will be described in detail.

The present invention provides a pharmaceutical composition for preventing or treating periodontal diseases comprising mangosteen extract.

In addition, the present invention provides a food or food additive composition, and an oral composition for preventing or improving periodontal diseases comprising mangosteen extract.

The mangosteen extract included in the composition according to the present invention is prepared from mangosteen which is a tropical fruit distributed in Malaysia, Thailand, Vietnam, Indonesia, etc. The mangosteen has been known to contain approximately 40 kinds of xanthone ingredients, and thus as a single kind of fruit, considerable amount of xanthone ingredients are contained.

The mangosteen extract can be purchased as commercially sold, or can be prepared by properly selecting extract ion methods and extract ion solvents commonly known in medical or food industrial fields without limitation. Common extraction methods can include ultrasonic extraction method, filtration method, and reflux extraction method, etc., but are not limited thereto. Preferably the mangosteen can be extracted using one or more extraction solvents selected from the group consisting of water and a lower alcohol having 1 to 6 carbon atoms. More preferably, since alpha-mangosteen and gamma-mangosteen which are active ingredients for periodontal disease among the mangosteen extracts are fat-soluble substances, water and hydrous organic solvent of ethanol such as below 50 to 100% of ethanol aqueous solution or ethanol solvent can be used. As one specific embodiment, the mangosteen extract used in the present invention can be collected by adding 3 to 5 part by weight of ethanol aqueous solution below 50 to 100% to 1 part by weight of mangosteen, extracting them for 8 to 10 hrs over refluxing at the temperature section of 60 to 80° C., filtering extracted solution by an appropriate filtration method like vacuum filtration using a filtration filter, etc., and removing extraction solvents under the condition of vacuum degree 0.2 to 0.5 atm.

Further, since such alpha-mangosteen and gamma-mangosteen are fat-soluble, they can be prepared as a water-soluble mangosteen molecular encapsulation which is a form of an inclusion compound through solubilization process to raise water solubility for effective formulation and internal absorbance.

As one specific embodiment, in order to prepare water-soluble mangosteen molecular encapsulation for increasing water solubility, stability and internal absorbance rate of fat-soluble mangosteen extracts, the mangosteen extracts can be molecular encapsulated by inclusion using inclusion compounds like cyclodextrin, preferably gamma-cyclodextrin, with additional active substances (for example, propolis, soybean unsaponifiable matter, lysozyme, vitamin-C) described below as needed. Preferably, the mangosteen extracts can be included at the temperature section of 60 to 80° C. in the range of 0.3 atm to 0.5 atm by mixing 0.2 to 0.5 part by weight of gamma-cyclodextrin to 1 part of weight of fat-soluble mangosteen extract. In case of need, in order to more stabilize included mangosteen extract, it can be stabilized by further adding 0.1 part of weight of arginine and storing at 4 degree or below for 4 hrs to 8 hrs, and it can be granulated by freeze-drying, etc.

Thus solubilized water-soluble mangosteen molecular encapsulation can be represented as a molecular encapsulation form having the structure shown in the following FIG. 1, and it can have approximately 50 to 150 nm of particle diameter.

As one preferable embodiment, the mangosteen extract can comprise one or more ingredients selected from the group consisting of xanthone ingredients, alpha-mangosteen and gamma-mangosteen having the structure of the following chemical formulas 1 and 2, respectively, as an active ingredient for prevention, improvement and treatment of periodontal diseases. More preferably, the composition according to the present invention can comprise the alpha-mangosteen and gamma-mangosteen together, and preferably the content ratio of alpha-mangosteen:gamma-mangosteen is 1:1 to 5:1, more preferably 2:1 to 4:1, the most preferably 8.75:2.54. In the range above, the composition according to the present invention shows excellent level of effects for prevention, improvement and treatment of periodontal diseases.

[Chemical formula 1]

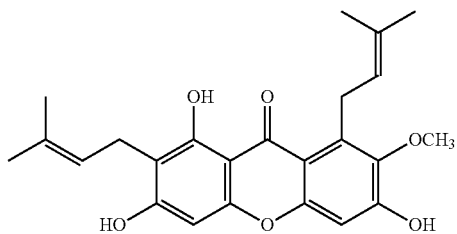

[Chemical formula 2]

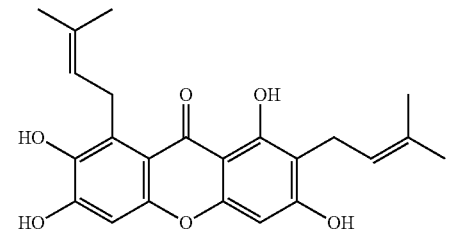

As one specific embodiment, in the composition according to the present invention, the mangosteen extract can be comprised in an amount of 30 to 50% by weight based on the weight of the total composition.

As one preferable embodiment, the composition according to the present invention can further comprises one or more active ingredients for periodontal diseases selected from the group consisting of propolis, lysozyme chloride, soybean unsaponifiable matter, vitamin C, xylitol and vitamin E, in order to give synergistic effects for periodontal diseases.

The "propolis" is a substance made by bees by mixing their saliva and enzymes, etc. to substances like gum extracted from various plants for their survival and reproduction, and it contains various ingredients such as flavonoid substances like flavone (for example, chrysin, tectochrysin, galangin) or flavanone (for example, quercetin, pinostrobin), aromatic acids like benzoic acid, coumarin benzylester, etc., cinnamic acid, pinobanksin, pinocembrin, etc., and it shows an antibacterial effect, an antimycotic effect, an effect for treating gastritis and gastric ulcer, an analgesic effect, an effect for reducing blood pressure and maintaining blood sugar, a protective effect for cardiac blood vessels, a protective effect for tooth. Preferably, the propolis can be comprised in an amount of 15 to 25% by weight based on the total weight of the composition according to the present invention.

The "soybean unsaponifiable matter" is hydrophobic as an ingredient existed in soybean oil, and it means a pure compound which does not make a soluble soap by responding a strong alkaline ingredient like potassium hydroxide, and it contains vegetable sterol (phytosterol). Specifically, the soybean unsaponifiable matter comprises ingredients such as beta-sitosterol, campesterol, stigmasterol, brassicasterol, resveratrol, lignin, genistein isoflavone, lecithin, phosphatidylcholine, sphingolipid, phosphatidyl serine. Preferably, the soybean unsaponifiable matter can be comprised in an amount of 7 to 13% by weight based on the total weight of the composition according to the present invention. Since this soybean unsaponifiable matter is a soft and white powder, has a unique smell, be not dissolved in water or an alcohol, and has a large volume, in case of comprising it in high capacity, there are disadvantages that its formulation is difficult, as not only filling is not going well but also it is melted by frictional heat during filling, and thereby ingredients of the total composition do not combine together well. Thus, as a preferable embodiment, the soybean unsaponifiable matter comprised in the present invention can be comprised in the composition by separate granulation from other ingredients of the composition. Further, as another preferable embodiment, it is preferable for useful formulation to granulate by including particularly spirits among various additives for such granulation. Various concentrations of spirits can be used as needed, but preferably 99.9%(v/v) of spirits can be used, and the weight ratio with the soybean unsaponifiable matter can be soybean unsaponifiable matter:spirits=5:1 to 1:1. More preferably, the weight ratio of soybean unsaponifiable matter:spirits can be 17:4.4.

The "lysozyme chloride" is mostly prepared by extraction from eggwhite as an enzyme cutting bacterial cell walls, performs an antibacterial action by modifying insoluble polysaccharides of bacterial and virus cell walls which are causative for gum diseases to soluble polysaccharides, shows an anti-inflammatory action around inflammation region, thereby inhibiting rubefaction, turgescence, symptoms, etc. and making pus released by decomposition, and not only treats inflammation by promoting tissue restoration around inflammation region but also shows an action preventing gum bleeding by an anti-heparin action. Preferably, the lysozyme can be comprised in an amount of 10 to 20% by weight based on the total weight of the composition according to the present invention.

The "vitamin C" is an anti-oxidant and it performs actions to prevent damages of cells by removing internal free radicals, to regenerate tissues of wounded areas rapidly by promoting synthesis of collagens, and to prevent gum bleeding by strengthening vessel walls and reviving actions of thrombin. Preferably, the vitamin C can be comprised in an amount of 3 to 10% by weight based on the total weight of the composition according to the present invention.

The "vitamin E" prevents damages of tissues by an anti-oxidant action through stabilization of cellular membranes, a microcirculation improvement action, etc., and it can be comprised in an amount of 0.5 to 2% by weight based on the total weight of the composition according to the present invention.

The "xylitol" is a sugar-alcohol natural sweetener extracted from birch or oak and a substance which can prevent proliferation of dental carries-related bacteria due to its pentose structure, and it can be comprised in an amount of 1 to 7% by weight based on the total weight of the composition according to the present invention.

More preferably, the composition according to the present invention can further comprise one or more ingredients selected from the group consisting of seaweed powder, dried yeast and chrome yeast, besides the additional ingredients above.

Meanwhile, since the active substance which shows effects for preventing, improving or treating periodontal diseases in the mangosteen extract is the alpha-mangosteen and/or gamma-mangosteen, the composition according to the present invention can comprise one or more selected from the group consisting of alpha-mangosteen and gamma-mangosteen as a pharmaceutical ingredient, instead of mangosteen extract itself. Thus, in case of comprising alpha-mangosteen and/or gamma-mangosteen, the additional ingredients can be comprised as same as the case of comprising the mangosteen extract as a pharmaceutical ingredient.

The composition of the present invention further comprises one or more pharmaceutically acceptable carriers besides active ingredients described above for administration. In the present invention, 'pharmaceutically acceptable carrier' means a known pharmaceutical excipient which is useful in case of formulating pharmaceutical active compounds for administration and is substantially non-toxic and non-sensitive under the conditions of use. The accurate ratio of this excipient is decided by standard pharmaceutical practices as well as solubility, chemical features, and selected administration route of active compounds.

The pharmaceutical composition of the present invention can be formulated as a proper form depending on desirable administration method using supplements such as an excipient, a disintegrating agent, a sweetening agent, a binging agent, a coating agent, an inflating agent, a lubricant, a glidant, a flavoring agent, etc.

The pharmaceutical composition can be formulated as a form of tablet, capsule, pill, granule, powder, injection or liquid medicine, but not limited thereto.

A formulation of pharmaceutical composition and a pharmaceutically acceptable carrier can be properly selected according to the known technology in the art, and for example, the following references can be referred: [Urquhart et al., Lancet, 16:367, 1980]; [Lieberman et al., PHARMACEUTICAL DOSAGE FORMS-DISPERSE SYSTEMS, 2nd ed., vol. 3, 1998]; [Ansel et al., PHARMACEUTICAL DOSAGE FORMS & DRUG DELIVERY SYSTEMS, 7th ed., 2000]; [Martindale, THE EXTRA PHARMACOPEIA, 31st ed.]; [Remington's PHARMACEUTICAL SCIENCES, 16th-20th editions]; [THE PHARMACOLOGICAL BASIS OF THERAPEUTICS, Goodman and Gilman, eds., 9th ed., 1996]; [Wilson and Gisvolds' TEXTBOOK OF ORGANIC MEDICINAL AND PHARMACEUTICAL CHEMISTRY, Delgado and Remers, eds., 10th ed., 1998].

The composition of the present invention can be orally administrated or non-orally administrated (for example, intravenous, subcutaneous, intra-abdominal, or local application) depending on the purposed method, and its dosage varies depending on weight, age, gender, physical condition, diet, administration time, administration method, excretion rate and severity of disease of a subject, etc. A daily dosage of the magnosteen extract is approximately 60 to 90 mg, and a daily dosage of alpha-mangosteen is approximately 7.5 to 9.0 mg on an adult basis, and that of gamma-mangosteen is 0.9 to 1.2 mg, and it is preferable to administrate it dividedly once to several times a day.

In case of using the composition according to the present invent ion for food, the food composition is a health functional food and it can be used through formulation itself or be comprised in other health functional foods as an additive of health functional food. The health functional food means food having body modulating function like prevention or improvement of diseases, biodefense, immunity, recovery of convalescence, aging inhibition, etc., and it should be harmless to human body when taking in a long term. The mixing amount of active ingredients can be properly decided depending on purpose of use (prevention, health or therapeutic treatment).

There is no particular limitation on the kind of the food. The examples of food where the above substances can be added are meat, sausage, bread, chocolates, candies, snack, cookies, pizza, ramen, other noodles, gum, dairy products including ice cream, sorts of soup, beverages, tea, drinks, alcohol beverages and vitamin complex, etc., and it includes all the health functional foods in the common sense.

The food composition of the present invention can comprise common ingredients used in preparation of food or food additives, specifically, a flavoring agent; a natural sweetener such as monosaccharides like glucose, fructose, disaccharides like maltose, sucrose, and dextrin, cyclodextrin as a natural carbohydrate, or a synthetic sweetener such as saccharin, aspartame; a nutrient; vitamin; electrolyte; a coloring agent; an organic acid; a protective colloid viscosity agent; pH regulator; a stabilizer; a preservative; glycerin; alcohol; a carbonating agent which is used on carbonated drinks, etc.

The composition according to the present invention can be used as an oral composition for an oral hygiene. In this case, it can have formulations of toothpaste, mouth freshener, mouth wash, gum massage cream, etc. Also, the combination ingredients of the oral composition provided in the present invention can be variously combined depending on uses and kinds of the composition besides ingredients described above.

Mode for Invention

Hereinafter, the present invention will be described in detail by the examples. However, the following examples are given for illustrating the present invention only, and the present invention is not limited by the following examples.

Hereinafter, the present invention will be described in detail by the examples to help understanding the present invention. However, the following examples are given for illustrating the present invention only, and the present invention is not limited by the following examples. The examples of the present invention are offered to describe the present invention more completely to those skilled in the art.

MANUFACTURING EXAMPLE 1

Preparation of Pulverized Mangosteen Pericarps 1 kg of Mangosteen pericarps were dried in a 25° C. ventilation dry oven, and they were made to 250 g of dried products whose moisture content is 10% or below. Then, they were pulverized using a crusher, and 230 g of pulverized mangosteen pericarps whose particle size is 400 mesh to 500 mesh were collected.

The content of active ingredients was analyzed by HPLC under following conditions.
  HPLC Analysis Conditions
  Column: Phenomenex Luna C18, 250×4.6 nm (5 um)
  Solvent: MeOH:H$_2$O:formic acid=90%:10%:0.1%
  Detector: UV/VIS, 254 nm
  Flow rate: 1.0 ml/min
  Column temp.: Heating Oven (35° C.)

As an analysis result, among 400 mesh to 500 mesh of pulverized mangosteen pericarps, the content of alpha-mangosteen was 3.0±1.0%, and that of gamma-mangosteen was 0.2±0.05%.

MANUFACTURING EXAMPLE 2

Preparation of Mangosteen Extracts Comprising Alpha-Mangosteen and Gamma-Mangosteen After 1 kg of pulverized mangosteen pericarps obtained by the preparation process of pulverized mangosteen pericarps according to the manufacturing example 1 were extracted at 60° C. for 4 hrs, using 10 L of ethanol, in a 20 L reactor, they were filtered using 1.0 μm filter paper, and their filtrate was concentrated under reduced pressure at 40° C., thereby obtaining 150 g of concentrates.

After 300 g of ethanol was injected in the 150 g of concentrates, and they were completely dissolved by increasing the temperature by 70° C., they were slowly crystallized at a cooling rate of 0.05 degree/min by 4° C., thereby crystals were precipitated. Then precipitated crystals were filtered.

By vacuum drying (vacuum conditions: 50° C., 0.3 atm, 8 hrs) and homogenization, 105 g of final mangosteen pericarp extracts were obtained. As a result of HPLC analysis under the same conditions as manufacturing example 1, the contents of alpha-mangosteen and gamma-mangosteen were as same as shown in the following table 1.

TABLE 1

| Mangosteen extract | Alpha-mangosteen | Gamma-mangosteen |
| --- | --- | --- |
| Content of active ingredient | 40.0 ± 5% | 5.0 ± 0.5% |

MANUFACTURING EXAMPLE 3

Preparation of Water-Soluble Mangosteen Molecular Encapsulations

According to combination ratio shown in the following table 2, water-soluble mangosteen molecular encapsulations where mangosteen extracts were solubilized were prepared. Specifically, 45 g of gamma-cyclodextrin was mixed to 150 g of fat-soluble mangosteen extracts obtained by the method of <manufacturing example 2>, and the mixture was stirred for 2 hrs at 1000 rpm of stir velocity under 0.4 atm of vacuum, thereby including mangosteen extracts. In order to stabilize included mangosteen extracts more, capsules were form-stabilized by adding 22 g of arginine and storing at 4° C. or below for 6 hrs. Then the solution was pulverized through freeze-drying (increasing temperature from −40° C. to 40° C., temperature increasing conditions: 1° C./hr).

As a result of measuring the contents of alpha-, gamma-mangosteen as index matters of water-soluble mangosteen molecular encapsulations prepared as shown above by the same method as the measuring method of manufacturing example 1, it is demonstrated that alpha-, gamma-mangosteen whose contents were same as shown in table 3 were contained.

TABLE 2

| Raw material name or generic name | Combination ratio(%) |
|---|---|
| Mangosteen extract powder | 7.00 |
| Gamma-cyclodextrin | 2.00 |
| Arginine | 1.00 |
| Purified water | 90.00 |
| Total | 100.00 |

TABLE 3

| alpha-mangosteen | gamma-mangosteen |
|---|---|
| 28.945 mg | 3.605 mg |

MANUFACTURING EXAMPLE 4

Preparation of Water-Soluble Mangosteen Composition

After putting 210 g of propolis extracts (liquid), 120 g of soybean unsaponifiable matter, 150 g of lysozyme chloride, 50 g of vitamin C, 10g of vitamin E, and 30 g of xylitol in 430 g of water-soluble mangosteen powder prepared in the manufacturing example 3, putting those in a powder mixer, and mixing fully, the powder was prepared by pulverization after drying properly in a vacuum drier (60° C., 0.4 atm, 8 hrs).

TABLE 4

| Contents of water-soluble mangosteen composition | |
|---|---|
| Raw material name or generic name | Combination ratio(%) |
| Water-soluble mangosteen molecular encapsulation powder | 43.0 |
| Propolis extract | 21.0 |
| soybean unsaponifiable matter | 12.0 |
| Lysozyme chloride | 15.0 |
| Vitamin C | 5.0 |
| Vitamin E | 1.0 |
| Xylitol | 3.0 |
| Total | 100.00 |

The prepared composition can be adapted to all food formulation including tablet, soft and hard capsules, liquid pouch, liquid vial, granules stick, etc.

EXAMPLE 1

Measurement of Antibiosis of Mangosteen Extracts Against *Streptococcus Mutans* (*Streptococcus Mutans* ATCC 25175)

Generally there are minimum inhibitory concentration (hereinafter, referred to MIC) test and time-kill assay test as test methods that become the standard for judging utility of antibiotics, when a new antibiotics is developed.

MIC TEST is a test method deciding minimum inhibitory concentration where bacteria cannot grow well, namely minimal usage of antibiotics for obtaining purposed antibacterial efficacy, and Time-Kill assay test is a test method deciding usage of antibiotics that can maintain purposed efficacy for certain time range. Each test was performed, in order to test whether mangosteem extracts have proliferation inhibiting efficacy against Streptocccus Mutans (*Streptocccus Mutans* ATCC 15175) to a certain degree.

(1) MIC Test for *Streptocccus Mutans*

MIC test for *Streptococcus mutans* (*Streptococcus mutans* ATCC 25175) was progressed according to the American clinical test standard method, NCCLS (National Committee for Clinical Laboratory Standards). To do comparative test of antibacterial ability of mangosteen extracts against *Streptococcus mutans*, after preparing each analysis sample as shown in the following table 5, that is the concentration of each analysis sample was 0, 1, 2, 3, 4, 5, 6, 7, 8, 9 and 10 ul, and the concentration of used *Streptococcus mutans* bacteria finally became $1\times10^5$ at the ratio of 50% by weight, and the concentration of DMSO (dimethyl sulfoxide) used as an analysis sample solvent finally became 1% by weight, and BHI medium (Brain heart infusion: Peptic Digest of Animal tissue, Sodium Chloride, Dextrose, Pancreatic Digest of Gelation, Disodium Phosphate, Final PH7.4+-0.2; Difco Company) was added for the remaining 40% by weight, they were used for the test.

As analysis samples, alpha- and gamma-mangosteen were used, which were obtained by adding over 99% of ethanol to mangosteen extracts prepared by the method of manufacturing example 2 and pulverized mangosteen pericarps prepared in the manufacturing example 1, dissolving and cooling them.

TABLE 5

| | Final concentration ratio (unit: μL) | | | | | | | | | | |
|---|---|---|---|---|---|---|---|---|---|---|---|
| S. mutans ATCC25175 | 50 | 50 | 50 | 50 | 50 | 50 | 50 | 50 | 50 | 50 | 50 |
| BHI medium | 40 | 40 | 40 | 40 | 40 | 40 | 40 | 40 | 40 | 40 | 40 |
| DMSO | 0 | 1 | 2 | 3 | 4 | 5 | 6 | 7 | 8 | 9 | 10 |
| Analysis sample | 10 | 9 | 8 | 7 | 6 | 5 | 4 | 3 | 2 | 1 | 0 |

After adding the samples in a microtube (duplicate) and culturing at 37° C. for 24 hrs, growth inhibit ion degree was observed by measuring absorbance at 500 nm. The result was same as the following table 6.

TABLE 6

| Analysis sample | MIC |
|---|---|
| Alpha-mangosteen | 1.0(ug/ml) |
| Gamma-mangosteen | 4.0(ug/ml) |
| Mangosteen extract | 10.0(ug/ml) |

As shown in the table 6, mangosteen extracts and alpha- and gamma-mangosteen isolated from thereto showed the antibacterial activity against *Streptococcus mutans* bacteria, which are periodontal diseases-related pathogenic bacteria, even at the very low concentration. In particular, alpha-mangosteen showed the antibacterial activity at only 1.0 ug/ml, and therefore it is considered to have the most excellent effect for prevention, improvement, and treatment of periodontal diseases.

(2) Time-Kill Assay Test for *Streptocccus Mutans*

The Time-kill assay test of analysis samples for *Streptococcus mutans* (*Streptococcus mutans* ATCC 25175) was performed according to a method of converting the initial 0.D550nm value versus the number of bacteria by McFarland Standard among methods based on NCCLS (National Committee for Clinical Laboratory Standards).

After the concentration of DMSO (dimethyl sulfoxide) used as an analysis sample solvent finally became 1% by weight, and BHI medium was added for the remaining 40% by weight, they were used for the test.

Specifically, 10 mg of mangosteen extract prepared in manufacturing example 2 was added, thereby preparing to 10,000 ug/ml. Then, after the concentration of DMSO (dimethyl sulfoxide) used as an analysis sample solvent finally became 10% by weight, and BHI medium was added for the remaining 40% by weight, they were used for the test. 10,000 ug/ml of mangosteen extracts prepared like this were diluted for the final concentration of mangosteen extracts to be 10, 100, 1000 ug/ml, respectively, according to the composition ratio as shown in the following table 7, thereby preparing test solutions. The used strain, *Streptococcus mutans* ATCC 25175 was controlled to finally become $1 \times 10^5$ CFU/ml at the ratio of 50% by weight.

TABLE 7

|  | Control group | Test group |
|---|---|---|
| S. mutans ATCC25175 | 50 | 50 |
| BHI medium | 40 | 40 |
| Analysis sample | 10(10% DMSO) | 10(10% DMSO + analysis sample) |

Then, as shown in the table 7, culturing 100 μl of test solutions prepared at the ratio per concentration under same conditions as MIC test, after collecting certain amount of test solutions direct, every 10 minutes, every 30 minutes, filming them to a solid BHI medium, and culturing at 37° C. for 48 hrs, the number of bacteria which formed colony. The result was described in the following table 8.

TABLE 8

|  | Control | 10 μg/mL | | | 100 μg/mL | | | 1,000 μg/mL | | |
|---|---|---|---|---|---|---|---|---|---|---|
|  |  | direct | 10 min | 30 min | Direct | 10 min | 30 min | direct | 10 min | 30 min |
| Number of bacteria | $1 \times 10^6$ | $9.0 \times 10^5$ | $9.0 \times 10^5$ | $9.0 \times 10^5$ | $9.0 \times 10^5$ | $7.0 \times 10^5$ | $3.0 \times 10^5$ | $6.0 \times 10^5$ | $1.0 \times 10^5$ | $2.0 \times 10^3$ |
| Survival rate (%) | 100 | 90 | 90 | 90 | 90 | 70 | 30 | 60 | 10 | 0.2 |
| Death rate (%) | 0 | 10 | 10 | 10 | 10 | 30 | 70 | 40 | 90 | 99.8 |

As described above, in case of using mangosteen extracts according to the present invention, more than 10% of periodontal diseases-related *Streptococcus mutans* bacteria were killed from right after treatment even at the extremely low concentration 10 ug/ml. In particular, in case of using 1000 ug/ml, it is demonstrated that the death rate was approximately 40% at right after treatment, and also over 90% after 10 min and most of bacteria after 30 min were killed.

EXAMPLE 2

Measurement of Antibiosis of Mangosteen Extracts Against *Porphyromonas Gingivalis* (*Porphyromonas Gingivalis* CCARM 0145)

The MIC test for *Porphyromonas gingivalis* (*Porphyromonas gingivalis* CCARM 0145) was performed by solid medium dilution method (Agar dilution method) of NCCLS (National Committee of Clinical Laboratory Standards, 1997).

Specifically, test bacterial solutions were prepared by suspending the strain activated by the logarithmic phase at absorbance (O.D550 nm) 0.5 in accordance with MacFarland standard in a medium where 5% sheep blood, 5 μg/ml of hemin and 0.5 μg/ml menadione were added in Trypticase soy agar (TSA).

The medium was prepared for the final concentration to be 0.25 μg/ml to 128 μg/ml, by serially diluting each sample in a medium where 5% hemolytic sheep blood, 5 μg/ml of hemin and 1 μg/ml of vitamin K1 were added to Brucella agar and mixing.

Approximately $5 \times 10^5$ CFU/spot of test bacterial solution was inoculated to the medium and it was cultured at 35° C. for 48 hrs under anaerobic conditions using GasPak EZ Anaerobic container System(Becton, Dickinson and Company, Sparks, Md., USA).

As a result, it is demonstrated that mangosteen extracts according to the present invention showed approximately 120 μg/ml of MIC for *Porphyromonas gingivalis* (*Porphyromonas gingivalis* CCARM 0145).

EXAMPLE 3

Measurement of Antibiosis of Mangosteen Extracts Against Various Bacterial Species for Periodontal Diseases In order to measure antibiosis of mangosteen extracts according to the present invention in more detail, for Prevotella intermedia KCOM 1107, *Fusbacterium nucleatum* subsp. polymorphum KCOM 1232, *Aggregatibacter actinomycetemcomitans* KCOM 1306 and *Porphyromonas gingivalis* ATCC 33277T, which are causative organisms for periodontal diseases isolated and identified from Koreans' mouths, minimum bactericidal concentration (MBC) was measured, thereby measuring antibiosis of mangosteen pericarp extracts.

The strains were all distributed from Korean Collection for Oral Microbiology (Gwangju, Korea) or American Type Culture Collection (ATCC, Manassas, Va., USA), and used.

The strains were inoculated to a medium where 0.5% yeast extract, 0.05% cysteine HCl—H2O, 0.5 mg/ml hemin and 2 ug/ml vitamin K1 were included in Tryptic Soy broth, and cultured in the 37° C. anaerobic chamber(Bactron I, Sheldon Manufacturing Inc., Cornelius, Oreg, USA) under anaerobic conditions (10% $H_2$, 5%$CO_2$, 85%$N_2$).

Micro-dilution method suggested in Clinical and Laboratory Standards Institute (CLSI) [1] was modified and used in MBC measurement. After bacteria were inoculated in the medium introduced above and cultured in a bacteria incubator at 37° C. for 24 hrs, they were diluted to be $1 \times 10^6$ CFU/ml and dispensed on a 96-well plate.

As an analysis substance, mangosteen extracts prepared in manufacturing example 2 as the composition described in the test group of the table 7 (MBL-Wmg 01), and water-soluble mangosteen extract molecular encapsulations prepared as the table 2 as the composition described in the test group of the table 7 (MBL-Wmg 01), respectively, were added to bacteria culture fluid to be diluted as 8 steps by 2 times from 2000 ug/ml.

Then the negative control group used only bacteria culture fluid, and the positive control group used a mouthwash sold commercially (Listerine®, Johnson & Johnson). After dispersing them by 200 ul to 96 well plates and culturing at 37° C. for 48 hrs, 10 ul was collected in the bacteria culture fluid, filmed to an agar medium, and cultured at 37° C. for 48 hrs. Then formed colonies were checked, thereby deciding the minimum concentration where bacteria did not grow 100%. Each reaction was repeated three times. The result showed in the following table 9 and FIG. 2 to FIG. 5.

TABLE 9

| Bacteria type | MBC (ug/ml) | | |
| --- | --- | --- | --- |
| | Mangosteen extract (MBL-Wmg 01) | Water-soluble mangosteen extract molecular encapsulation (MBL-Wmg 02) | Lysterine |
| Prevotella intermedia KCOM 1107 | 1,000 | 62.5 | 1/8 |
| Fusbacterium nucleatum subsp. polymorphum KCOM 1232 | 2,000 | 250 | 1/4 |
| Aggregatibacter actinomycetemcomitans KCOM 1306 | >2,000 | >2,000 | 1/4 |
| Porphyromonas gingivalis ATCC 33277T | 125 | 62.5 | ND |

*ND: Not determined

As can be seen from the result of the table 9, water-soluble mangosteen extract molecular encapsulations (MBL-Wmg 02) showed stronger antibacterial effects 16 times, 4 times, and twice, respectively, for Prevotella intermedia KCOM 1107, Fusbacterium nucleatum subsp. polymorphum KCOM 1232 and Porphyromonas gingivalis ATCC 33277T, which belong to major causative bacterial species for periodontal diseases, than mangosteen extracts (MBL-Wmg 01). However, bot substances did not show antibacterial ability at the maximum concentration (2 mg/ml) and below for Aggregatibacter actinomycetemcomitans KCOM 1306.

When referring that A. actinomycetemcomitans bacterial species is a major pathogenic bacterial species for particular periodontal diseases like periodontitis before adolescence, and P. intermedia, F. nucleatum and P. gingivalis belong to major pathogenic bacterial species in adult periodontitis which belongs to most periondontal diseases, mangosteen pericarp extracts according to the present invention, MBL-Wmg 01 and MBL-Wmg 02 can be highly effectively used for food additives, oral hygiene items(toothpaste, gargle, etc.) and health functional food for preventing periodontal diseases at not less than 2.0 mg/ml and 250 µg/ml concentration, respectively.

In so far, as the specific part of the present invention has been described in detail, for those skilled in the art, it is clear that this specific description is merely a preferred example, and the scope of the present invent ion is not limited by that. Accordingly, the substantive scope of the present invent ion is defined by the following claims and the equivalents thereto.

The invention claimed is:

1. A method for treating or improving periodontal diseases induced by *Prevotella intermedia* and *Fusbacterium nucleatum*, comprising administering extract of mangosteen, which comprises a daily dosage of 7.5 to 9.0 mg of alpha-mangosteen together with propolis, lysozyme chloride, soybean unsaponifiable matter, vitamin C, xylitol, and vitamin E.

2. The method of claim 1, wherein the extract of mangosteen is characterized by extracting shells of mangosteen with one or more solvents selected from the group consisting of water, an alcohol having 1 to 6 carbon atoms, and a mixed solvent of water and an alcohol having 1 to 6 carbon atoms.

3. The method of claim 2, wherein the alcohol having 1 to 6 carbon atoms is ethanol.

4. The method of claim 1, wherein the extract of mangosteen is a water-soluble extract of mangosteen further comprising gamma-dextrin as a molecular encapsulation coating agent.

5. The method of claim 1, further administering one or more ingredients selected from the group consisting of seaweed powder, dried yeast and chrome yeast.

6. The method of claim 1, wherein the extract of mangosteen is administered in a form of a pharmaceutical composition, a food composition, or an oral hygiene composition.

* * * * *